(12) United States Patent
Sulamanidze et al.

(10) Patent No.: US 7,513,904 B2
(45) Date of Patent: Apr. 7, 2009

(54) SURGICAL THREAD AND COSMETIC SURGERY METHOD

(76) Inventors: Marlen Andreevich Sulamanidze, d. 27, kv. 67, ul. Nagatinskaya, 115533 Moscow (RU); Georgiih Marlenovich Sulamanidze, d. 27, kv. 67, ul. Nagatinskaya, 115533 Moscow (RU)

( * ) Notice: Subject to any disclaimer, the term of this patent is extended or adjusted under 35 U.S.C. 154(b) by 90 days.

(21) Appl. No.: 10/592,986

(22) PCT Filed: Mar. 15, 2004

(86) PCT No.: PCT/RU2004/000095

§ 371 (c)(1),
(2), (4) Date: Sep. 14, 2006

(87) PCT Pub. No.: WO2005/087283

PCT Pub. Date: Sep. 22, 2005

(65) Prior Publication Data

US 2007/0167958 A1     Jul. 19, 2007

(51) Int. Cl.
*A61B 17/06* (2006.01)
(52) U.S. Cl. .................................. 606/224; 606/204.35
(58) Field of Classification Search ................. 606/222, 606/224, 228; 623/23.72; 112/222, 302
See application file for complete search history.

(56) References Cited

U.S. PATENT DOCUMENTS 5,217,494 A * 6/1993 Coggins et al. .......... 623/23.72
5,810,851 A * 9/1998 Yoon .......................... 606/148
6,485,504 B1 * 11/2002 Johnson et al. ............. 606/216
6,663,633 B1 * 12/2003 Pierson, III .................. 606/72
2003/0074021 A1 * 4/2003 Morriss et al. .............. 606/215
2007/0233276 A1 * 10/2007 Conrad et al. ............. 623/23.72

FOREIGN PATENT DOCUMENTS

| RU | 2 121 311 | 11/1998 |
| RU | 2 135 109 | 8/1999 |
| RU | 2 139 734 | 10/1999 |
| RU | 2 195 186 | 8/2002 |
| WO | WO 03/103972 | 12/2003 |

* cited by examiner

*Primary Examiner*—Todd E Manahan
*Assistant Examiner*—Eric Blatt
(74) *Attorney, Agent, or Firm*—Bachman & LaPointe, P.C.

(57) ABSTRACT

A surgical thread is made of a metal, polymer or biological material embodied in the form of a spiral whose diameter ranges from 0.5 to 5 mm. The thread has a diameter ranging from 0.1 to 1 mm and exhibits the properties of a compression or extension spring obtainable by heat treatment. Also a method is disclosed which is characterized in that it consists in introducing the spiral-shaped thread into subcutaneous soft tissues in order to tighten and fix said tissues by means of a puncture needle in bore of which a thread-spiral exhibiting the properties of a compression or extension spring is fixed from outside or from inside. When the needle is extracted the thread-spiral remains under skin preserving the compression or extension properties thereof, thereby producing a skin compression or extension effect.

3 Claims, 3 Drawing Sheets

SURGICAL THREAD AND COSMETIC SURGERY METHOD

CROSS REFERENCE TO RELATED APPLICATIONS

This case is the U.S. national phase of International Application No. PCT/RU2004/000095 filed Mar. 15, 2004.

BACKGROUND OF THE INVENTION

The invention concerns the field of medicine, materials and methods for esthetic surgery. In particular, the invention concerns medical materials used in plastic surgery in cosmetic operations.

PRIOR ART

Surgical threads for cosmetic surgery are known, they are manufactured from various materials: metal, polymer, and biological materials. The general characteristics of the threads are: toughness, a smooth surface, biological inactivity. Recently, threads with microscopic angular protrusions have been suggested and used, which allow to run the threads through the tissues in one direction only.

Depending on the character of the surgery, various surgical threads are used. These are wire threads: of tantalum, gold, nickel and others. Non-metallic threads used are manufactured of lavsan, nylon, capron, polypropylene, vicryl, polysorb, and other materials.

A correction of facial wrinkles when the elasticity of the skin is diminished and lost and ptosis (hanging) of soft tissues is one of the basic problems of cosmetic surgery. To this end, surgical threads without protrusions are utilized in esthetic surgery only to lay surgical sutures in open wounds. Thus, dislocated soft tissues can only be tightened and sewn up after corresponding cuts have been made and skin-fat patches have been mobilized.

Threads with protrusions allow to tighten and fix soft tissues without surgical cuts. Methods for placing such threads through skin punctures by means of special needles have been devised and are used. Such interventions enable to obtain a sufficiently good tightening of the soft tissues of the lateral areas of the eyebrows, the areas of the cheekbone, mental and submental areas and to create good esthetic outlines of these parts of the face. This is achieved because in these areas of the face there is little activity of the muscles effecting chewing and facial expression, so that the protrusions are not affected by them and the fixation of the tightened tissues is stable. Moreover when such threads are arranged in places where an activity of the muscles takes place they do not yield lasting and stable results: In the next 10-14 days following their deployment, a relapse occurs, i.e. a dislocation of the soft tissues, since the natural activity of the muscles leads to a weakening of the protrusions and even causes them to be torn off. These are:

the forehead area for lifting the eyebrows and the area of the nose bridge, and together with them the skin of the upper eyelids;

the corner of the mouth for lifting the soft tissues of the areas around the mouth and for removing "worry" wrinkles;

the cheeks, for lifting the soft tissues of these areas;

the neck, for lifting the neck skin and to straighten out wrinkles of the neck skin.

The closest to the invention in terms of subject matter are the surgical threads for cosmetic surgery according to WO 03/103733. These threads are manufactured with notches on their surface, the notches being made with the objective of using these threads.

SUMMARY OF THE INVENTION

The objective of the invention is achieved in that a thread for cosmetic surgery, manufactured from a metal, polymer or biological material with elements for fixing subcutaneous tissues is manufactured in a helical shape in the form of a compression or extension spring having an outer diameter of the helix of 0.5 to 5 mm and a thread material diameter of 0.1 to 1 mm. The method for carrying out cosmetic surgery using the surgical thread comprising its introduction into subcutaneous tissues with the aim of tightening and fixing them is characterized in that the helix shaped thread in the form of a compression or extension spring is attached with its front end to the sharp end of a puncture needle, the thread is tightly wound on the needle and the needle with the thread is introduced in an extended state along the body of the needle as a compression spring and in a compressed state as an extension spring, into a subcutaneous cell following a marked outline, and after reappearance of the needle, the thread is unfastened, the needle is completely extracted, while the thread remains subcutaneous in a stressed state with a tendency to compress or extend under the influence of spring properties, the subcutaneous fat cell compresses in accordance with the state of the thread, thus creating an effect of tightening ptosis-affected tissues, wherein the needle is turned during its introduction following the loop windings of the thread, while it is turned in the opposite direction during its extraction. According to another version of introducing the thread into subcutaneous tissues, its fastening can be carried out in the opening of the puncture needle with a gap between the diameter of the helix and the inner wall of the needle of the order of 0.2 mm to 2 mm.

Depending on the character of the operation, subcutaneous tissues can be fixed in an intended area. To this end, two parallel threads are introduced, then their ends are moved towards each other, joined to one another, sunk underneath the skin, and an integral construction is created, tightening the ptosis-affected tissues.

BRIEF DESCRIPTION OF THE DRAWINGS

Hereinafter the invention will be explained by drawings, in which.

DETAILED DESCRIPTION

Figure 1:
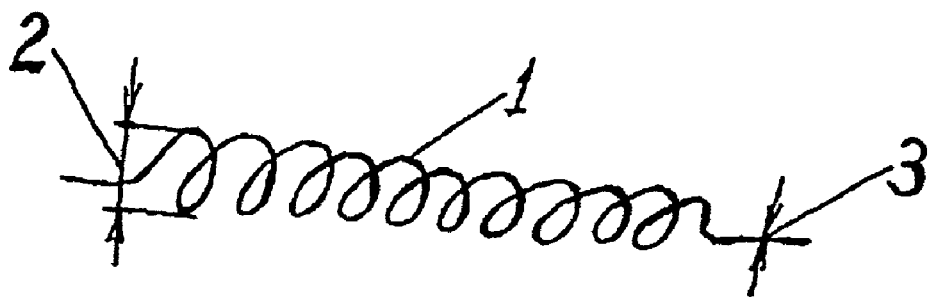
FIG. 1 shows a helix shaped surgical thread.
Figure 2:
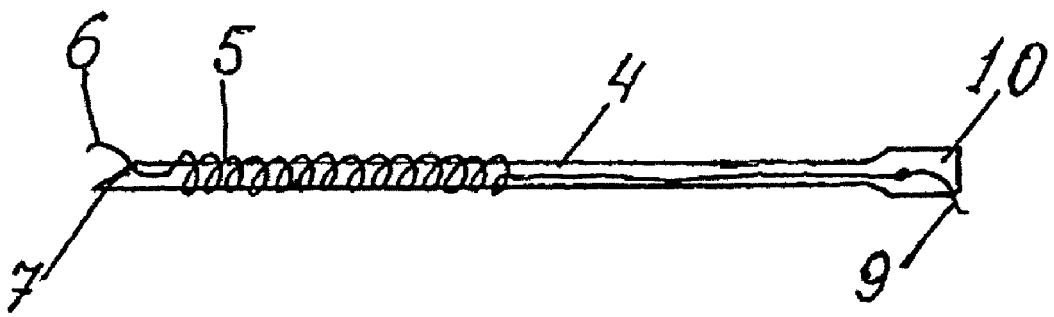
FIG. 2 shows the thread wound around a thin injection needle from the outside.
Figure 3:
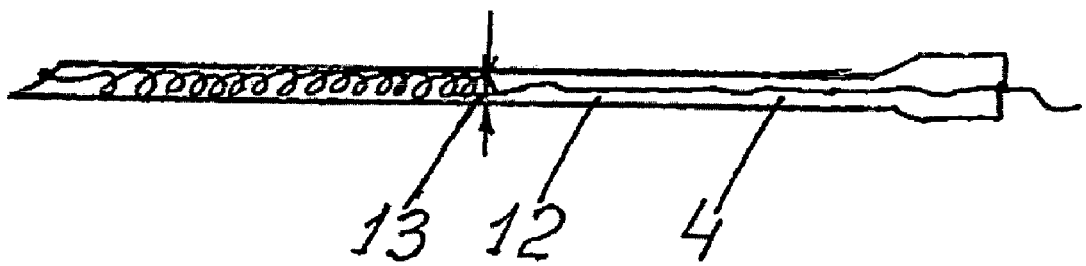
FIG. 3 shows the thread introduced into the opening of a thick injection needle.
Figure 4:
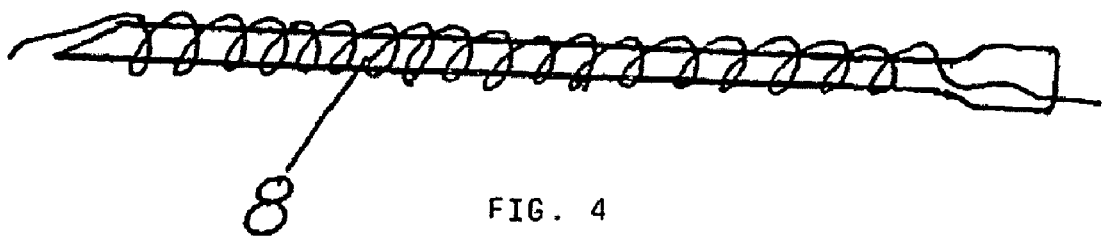
FIG. 4 shows the thread in an extended state prior to its introduction into the subcutaneous soft tissues.
Figure 5:
FIG. 5 shows the needle with the helix thread introduced subcutaneously.
Figure 6:
FIG. 6 shows the state of the thread when the puncture needle has been extracted.
Figure 7:
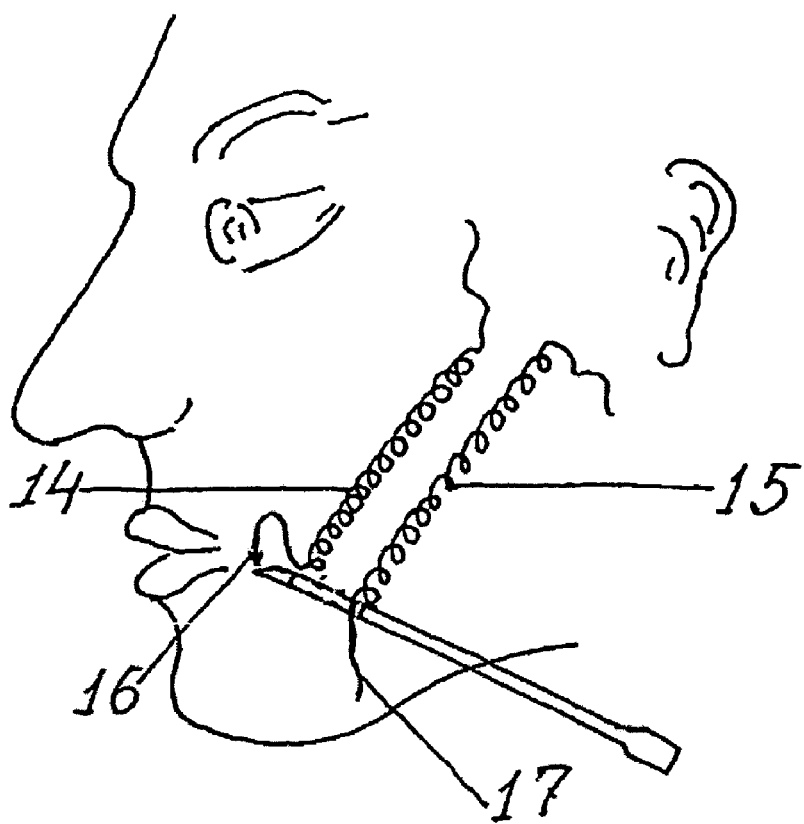
FIG. 7 shows two parallel threads introduced subcutaneously and their connection with one another.
Figure 8:
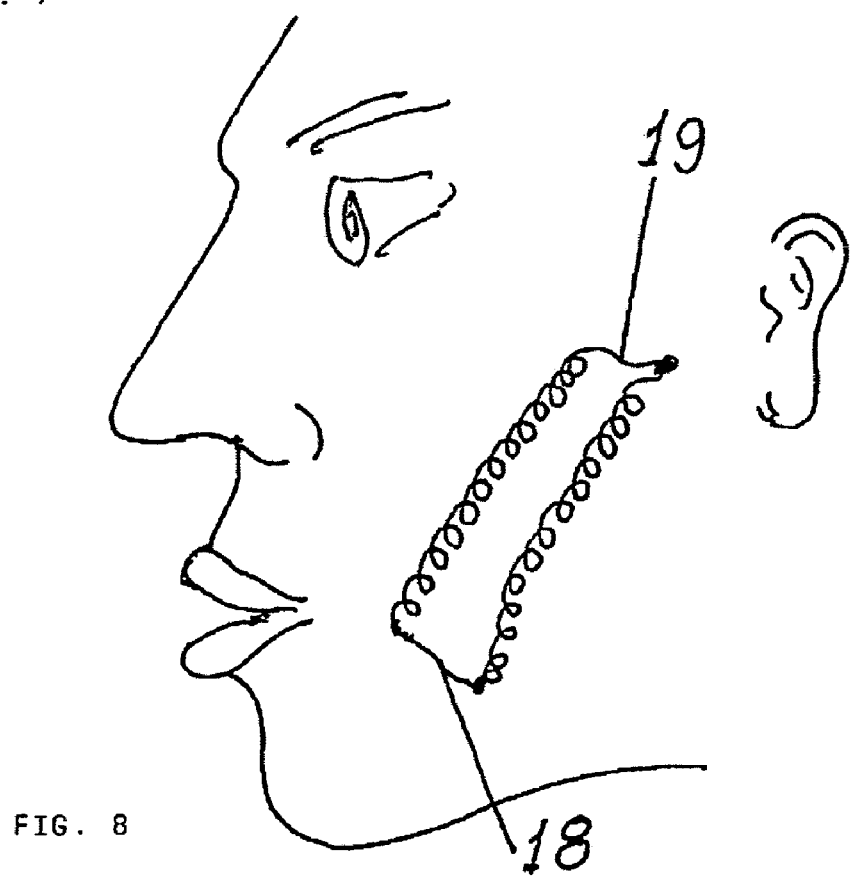
FIG. 8 shows two joint threads defining an integral construction tightening the ptosis-affected tissues.

The helix shaped surgical thread 1 is manufactured from a metal, polymer or biological material. Depending on the character of the cosmetic operation, threads of various dimensions are used. The diameter 2 of the helix can range from 0.5 to 5 mm, while the diameter of the material 3 of the thread can range from 0.1 mm to 1 mm. The character of the operation determines the use of threads of the corresponding materials. The surgical thread-helixes are made with properties of compression or extension springs. The threads are provided with spring properties by means of heat treatment, varying in accordance with the thread material.

The wide range of cosmetic operations and of the places where they are carried out in a patient also demand different methods of their implementation. The helix shaped thread is introduced into the subcutaneous soft tissues by means of the puncture needle 4. The thread is wound on the thin needle from the outside in such a way that each loop 5 tightly abuts the neighboring loops. The front end 6 of the thread is fastened to the sharp end 7 of the needle. When the helix is introduced with the properties of the compression spring, it is extended along the body 8 of the needle by 2-3 times, and the second end 9 of the thread is fastened to the other end 10 of the puncture needle 4. If the helix relaxes, it remains short.

In the extended state, the thread-helix is introduced subcutaneously into the soft tissues in the following manner:

The skin is punctuated by the sharp end of the needle, and the needle is drawn subcutaneously along a previously marked outline, wherein it is helix introduced in the manner of a gimlet, turning along the winding of the loop 5 of the thread. In the required place the sharp end of the needle 4 reappears on the surface of the skin 11 and the end of the thread 9 is held by pincers or a clamp. Further, the needle is completely extracted from the subcutaneous cell carefully in helical movements but in the opposite direction with respect to its introduction, while the thread-spring 1 remains subcutaneous in a stressed state, that is, with a tendency to compress under the influence of the spring properties. According to the state of the thread the subcutaneous fat cell is compressed, thus creating a tightening effect on the ptosis-affected tissues.

Another operation method is characterized in that the thread-helix 1 is placed in the opening 12 of the puncture needle 4 with a gap 13 between the diameter of the helix and the inner wall of the needle of the order of 0.2 mm to 2 mm, and the needle with the thread is introduced into the subcutaneous tissues. In the described methods, the application of the thread-helix can be carried out with the properties of a compression and extension spring. When using the thread-helix with the properties of an extension spring, it is compressed during the subcutaneous introduction into the soft tissues, while after the extraction of the needle the thread-helixes with the tendency to extend remains in the subcutaneous soft tissues.

Another example of the application of the method consists in that two thread-helixs 14, 15 are introduced subcutaneously in parallel, thereafter their ends 16, 17 are guided towards each other subcutaneously, are joined at 18, 19 and form an integral construction tightening the ptosis-affected tissues. This intervention makes it possible to evenly tighten the soft tissues in an upward direction and thereby obtain an effect of straightening out wrinkles and creases of the skin. The movements of the face skin caused by facial expression, the process of chewing food and even a skin massage do not result in a loss of the obtained effect, since the thread-springs in the subcutaneous cell extend and compress together with the extension and compression of the skin, retaining their previous form. Thereafter these threads are covered with fibrous tissue which helps to stabilize the obtained effect. A number of these threads introduced subcutaneously in the required sections of the ageing face create a rejuvenating effect.

INDUSTRIAL APPLICABILITY

As shown in the description, the invention can be utilized widely in various cosmetic and plastic surgery operations either alone or in combination with other surgical interventions.

When using helix-shaped threads, in many cases the necessity to do major surgical operations of the rhytidoplastic type will no longer arise. Interventions utilizing such threads are easy and bloodless, they do not leave scars, can be done ambulatory under local anesthetic and with a short recovery time. They can be combined with planting threads with notches and other minimally invasive interventions and procedures which are applied in cosmetic surgery.

The invention claimed is:

1. A method for carrying out cosmetic surgery operations utilizing a surgical thread (1) for cosmetic surgery, a surgical thread for cosmetic surgery comprising a thread having elements for fixing subcutaneous tissue, said elements comprise a helix shape in the form of a spring, said thread having a diameter of between 0.1 mm to 1.0, and said helix shaped elements having a diameter of between 0.5 to 5 mm, wherein said thread is formed of a material selected from the group consisting of metal, polymer, biological, and mixtures thereof, the method comprises the steps of:
   (a) fastening of the helix-shaped thread (1) at its front end (6) to a sharp end (7) of a rectilinear puncture needle (4);
   (b) winding the thread (1) tightly around the rectilinear puncture needle (4);
   (c) introducing the needle (4) with the thread (1) into a subcutaneous cell following a marked outline, wherein the needle (4) is turned during its introduction following the loop windings of the thread (1);
   (d) unfastening the thread (1) after reappearance of the rectilinear puncture needle (4); and
   (e) completely extracting the needle (4), wherein the rectilinear puncture needle (4) is turned during its extraction in the opposite direction compared with its introduction, while the thread (1) remains subcutaneous in a stressed state with a tendency to compress or extend under the influence of spring properties, wherein the subcutaneous fat cell compresses in accordance with the state of the thread (1), thus creating an effect of tightening ptosis-affected tissues.

2. A method for carrying out cosmetic surgery operations utilizing a surgical thread (1) for cosmetic surgery, a surgical thread for cosmetic surgery comprising a thread having elements for fixing subcutaneous tissue, said elements comprise a helix shape in the form of a spring, said thread having a diameter of between 0.1 mm to 1 mm and said helix shaped elements having a diameter of between 0.5 to 5 mm, wherein said thread is formed of a material selected from the group consisting of metal, polymer, biological, and mixtures thereof, the method comprises the steps of:
   (a) fastening of the helix-shaped thread (1) in the form of a spring at its front end (6) to a sharp end (7) of a rectilinear puncture needle (4);
   (b) fastening of the helix-shaped thread (1) in an opening (12) of the rectilinear puncture needle (4) with a gap (13) between the diameter of the helix and the inner wall of the rectilinear puncture needle of the order of 0.2 mm to 2 mm;

(c) introducing the needle (4) with the thread (1) in an extended state along the body of the rectilinear puncture needle (4) as a compression spring or in a compressed state as an extension spring, into a subcutaneous cell following a marked outline, wherein the needle (4) is turned during its introduction following the loop windings of the thread (1);

(d) unfastening the thread (1) after reappearance of the rectilinear puncture needle (4);

(e) completely extracting the needle (4), wherein the rectilinear puncture needle (4) is turned during its extraction in the opposite direction compared with its introduction, while the thread (1) remains subcutaneous in a stressed state with a tendency to compress or extend under the influence of spring properties, wherein the subcutaneous fat cell compresses in accordance with the state of the thread (1), thus creating an effect of tightening ptosis-affected tissues.

3. Method according to claim 1 or 2, wherein two threads (14, 15) are introduced into the subcutaneous tissues in parallel following a marked outline, whereafter their ends (16, 17) are guided toward each other, joined to one another, sunk into the skin, forming an integral construction tightening the ptosis-affected tissues.

* * * * *